United States Patent
Strong

Patent Number: 5,523,134
Date of Patent: Jun. 4, 1996

[54] LIQUID FILLED SURGICAL PACKS

[76] Inventor: John E. Strong, 29W025 Geneva Rd., West Chicago, Ill. 60185-3201

[21] Appl. No.: 267,011

[22] Filed: Jun. 16, 1994

[51] Int. Cl.$^6$ ............................ A61B 19/00; A61M 29/00
[52] U.S. Cl. .................. 428/35.2; 428/36.8; 428/494; 206/438; 383/113; 383/116; 383/119; 383/901; 600/37; 604/96; 606/192
[58] Field of Search .................. 428/36.8, 35.2, 428/492, 494, 519, 520; 128/DIG. 24, 20, 899, 897, 898; 600/37, 206; 206/438; 383/116, 119, 901, 113; 607/113, 114; 606/192, 194, 195, 196; 604/96, 282

[56] References Cited

U.S. PATENT DOCUMENTS

| | | | |
|---|---|---|---|
| 2,697,424 | 12/1954 | Hanna | 383/901 |
| 4,499,154 | 2/1985 | James et al. | 428/494 |
| 4,548,844 | 10/1985 | Podell et al. | 428/35.2 |
| 4,575,476 | 3/1986 | Podell et al. | 428/494 |
| 4,819,637 | 4/1989 | Dormandy, Jr. et al. | 606/195 |
| 5,023,119 | 6/1991 | Yamakoshi | 428/35.2 |
| 5,080,088 | 1/1992 | Le Vahn | 600/206 |

Primary Examiner—Ellis P. Robinson
Assistant Examiner—Rena L. Dye
Attorney, Agent, or Firm—Banner & Allegretti, Ltd.

[57] ABSTRACT

A flexible abdominal pack for displacing organs during surgery which is nonabrasive, free of foreign bodies and which conforms to the organ being displaced. The pack is sausage shaped and the walls are formed from cured latex having a cured lubricous hydrogel coating on the surface thereof.

5 Claims, 1 Drawing Sheet

U.S. Patent  Jun. 4, 1996  5,523,134
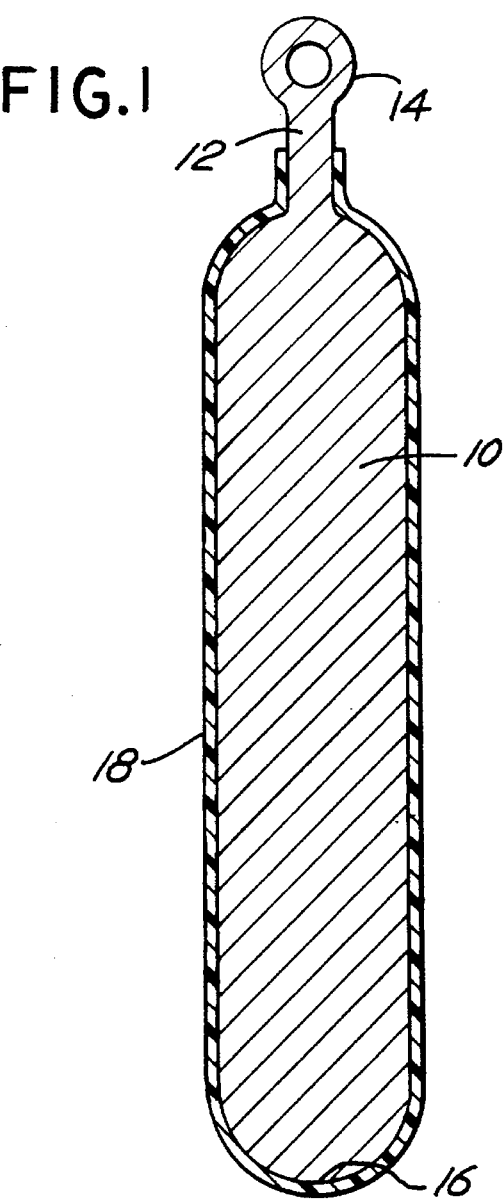
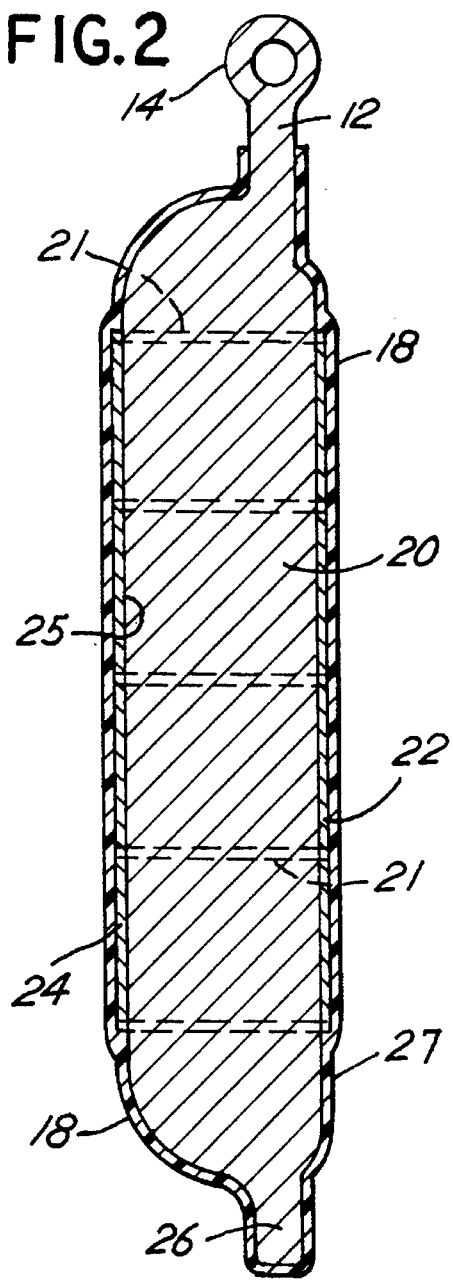
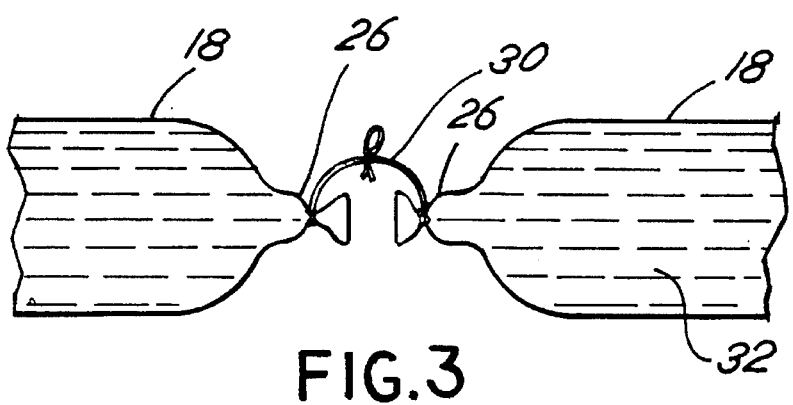

LIQUID FILLED SURGICAL PACKS

This invention relates to surgical packs in the form of saline-filled tubes or pillows made from an elastomer having a smooth lubricous surface free of foreign bodies likely to bring about formation of adhesions, and to a method for performing a surgical procedure using these surgical packs.

BACKGROUND OF THE INVENTION

In performing abdominal surgery on the pancreas, liver, uterus and other internal organs it is necessary to displace temporarily the intestines which block the view of the organ being treated and interfere with the surgeon's manipulation of the operative instruments. It is also necessary to remove the intestines from the operative site to prevent them from accidentally being cut or otherwise damaged.

PRIOR ART

At present, it is the customary procedure of surgeons to use a plurality of cotton or gauze packs soaked in sterile saline solution to displace the intestines. The cotton fabric is rough and abrades the organs (bowel, liver, bladder, uterus, ovaries) in contact therewith. Often particles of gauze and/or cotton are left in the abdomen. Both gauze and cotton sponges are known to be abrasive, even when handled gently. Medical literature establishes that cotton particles can cause recurrent and/or adhesive disease with a 50% chance that further surgery is required. Abrasion frequently results in the formation of adhesions in the peritoneal cavity, for example.

Another problem with using multiple cotton packs or lap sponges is that occasionally the surgeon fails to remove one after completing an operation. A radioactive strip is applied to some sponges to make then x-ray detectable so that they are not iatrogenically left in the abdomen.

SUMMARY OF THE INVENTION

The object of the invention is to provide elastomeric surgical packs having a smooth lubricous surface which can be used as a restraint for intestines during abdominal surgery which obviate the problems associated with fibrous cotton sponges. The packs of the invention are filled with saline solution and conform gently to the organs in contact therewith like a pillow.

Another object is to provide a method for conducting abdominal surgery using such elastomeric packs in which the intestines are displaced into the upper abdominal cavity and away from the abdominal side walls in a nonabrasive gentle manner.

The surgical packs in accordance with the invention consist of one or more tubular cushions made from an elastomer and having a lubricous surface which is smooth and nonabrading. Several tubular cushions are interconnected laterally and are filled with saline solution. It is important that the elastomeric material be devoid of any powder coating such as corn starch, talc or zinc oxide, normally used on latex gloves and the like to make the surface slippery since these dusting powders are known to give rise to the formation of granulomas and subsequent peritonitis.

The preferred material for the surgical packs is a latex elastomer, natural or synthetic, having a hydrophilic hydrogel-forming polymer coating bonded to the external surface thereof. These coatings are well known in the art. The preferred hydrogel polymer for use in the invention is a copolymer of 2-hydroxyethyl methacrylate with methacrylic acid or 2-ethylhexyl acrylate. The lubricity of the polymer surface may be improved by the addition of an ionic or cationic surfactant, e.g., an N-lauryl or N-cetyl pyridinium chloride. The tubular cushions of the invention are prepared by dipping a former of the desired shape in liquid latex, priming the rubber tubular article with a dilute acid, and dipping the primed article in a solution of the hydrogel-forming polymer containing a curing agent. The rubber and polymer are subsequently dried and cured/vulcanized at elevated temperature. The hydrogel polymer contains mainly 2-hydroxyethyl methacrylate and methacrylic acid. If a surfactant is used, it is applied prior to curing. The hydrogel provides a non-tacky surface. These coatings and methods for forming articles from hydrogel-coated elastomers is described in U.S. Pat. Nos. 4,499,154 and 4,575,476 incorporated herein by reference.

These hydrogel polymers are well known for use as contact lenses and have been proved to be non-reactive.

Examples of other suitable hydrogel polymers are polyvinyl pyrolidone, polyhydroxy ethylacrylate or methacrylate, polyhydroxy propyl acrylate or methacrylate, and copolymers of these with each other or with acrylic or methacrylic acid, acrylic or methacrylic esters or vinyl pyridine.

The surgical packs of the invention are generally sausage shaped and terminate at the ends in necks which can be used to fill the packs with saline solution and to tie them together. The packs may be packaged in sterile envelopes and filled in the operating room, or to save time may be prefilled. By tying the packs together, they can be removed together at the end of the procedure without fear of leaving one behind. Instead of multiple cotton sponges, three of the hydrogel coated elastomeric packs tied together are used to displace the intestines into the upper abdominal cavity and away from the side walls of the abdominal cavity. One pack is disposed centrally and the other two are disposed laterally against the intestines.

The packs are held in place by the blades of an abdominal retractor commonly used in surgery. A suitable instrument is sold commercially by Codman division of Johnson & Johnson.

The packs are preferably flat on the exposed sides which are in contact with the blades of the retractor. The lateral packs may be gently curved longitudinally to conform to the side wall of the abdominal cavity and/or the intestines being restrained. Since the elastomeric walls are flexible, they will conform essentially to force applied. In order to provide packs which have and retain a predetermined shape, the tubular pack can be formed by dipping into latex a former of the desired shape having reinforcing ribs on the surface thereof. The ribs are semi-rigid and may be formed of polypropylene, for example. The latex film builds up on the former over the ribs which reinforce the latex walls of the pack.

BRIEF DESCRIPTION OF THE DRAWINGS

Formers for preparing the surgical packs of the invention are illustrated in the accompanying drawings in which FIG. 1 is a longitudinal section through a former showing a latex/hydrogel film on the surface thereof.

FIG. 2 is a similar view through a former encased in reinforcing ribs and covered with latex/hydrogel.

FIG. 3 is a side view of the ends of a pair of surgical packs containing saline solution and tied together.

DESCRIPTION OF PREFERRED EMBODIMENTS

Referring to FIG. 1, the former 10 is shaped like a cylinder with a lower rounded end 16 and a neck 12 at the upper end. The former is suspended from an eye 14 at the upper end. A latex/hydrogel film 18 covers the surface of the former. Latex layers are built up by dipping, and the final coat is the hydrogel polymer. After curing, the externally-coated elastomer is stripped from the former. Prior to use, it is filled with saline solution and the neck is closed with a suitable clamp or the like.

FIG. 2 shows a former 20 which is enclosed in a frame-like rib structure comprising a series of longitudinal, peripherally-spaced ribs 22, 24 connected together by peripheral rings 21 on the outer surface of the former. Former 20 has a flat side 27 and a rounded side 25. The form includes a neck 12 at the upper end thereof. The rib structure and former are covered over with latex/hydrogel elastomer 18 by dipping, as disclosed in U.S. Pat. No. 4,575,476. The ribs are made from polypropylene extruded strips, or similar material, joined together by welding or suitable adhesive. After curing, the latex pack or pillow is removed from the former together with the reinforcing cage 21, 22, 24. The closed end of the neck 26 is snipped off so that the pack can be filled with saline solution. The rib structure reinforces the pack so that it maintains its shape in use but without being rigid.

FIG. 3 shows two reinforced abdominal packs which have been removed from the former of FIG. 2, filled with saline solution 32, and tied together with nylon cord 30 which also ties off the necks 26 of the packs.

The latex may be natural rubber, butadiene-styrene, or similar synthetic rubber. The hydrogel on the outer surface of the latex is smooth and lubricous. It does not abrade the organs in contact with the pack even when there is continued relative movement between the packs and organ. Thus, adhesions resulting from abrasion with rough cotton conventionally used are avoided. Tying the packs together at their necks assures removal of all the packs when the procedure has been completed.

I claim:

1. A surgical abdominal cavity pack for displacing, temporarily, selected organs within the abdomen during surgery, which pack is nonabrasive, free of foreign bodies, and conforms to the organ being displaced, comprising a plurality of hollow elongated cylindrical tubes having at least one filler neck at one end which is of smaller diameter than said tube, the walls of said tubes being formed from a cured elastomer having a cured lubricous hydrogel coating on the external surface thereof, said tubes being filled with saline solution and tied together at said filler necks.

2. The abdominal pack of claim 1 in which said hydrogel coating is a copolymer of 2-hydroxy ethyl methacrylate and methacrylic acid.

3. The abdominal pack of claim 1 in which said cylindrical tubes have one structurally flattened side and is internally reinforced to maintain its shape.

4. The abdominal pack of claim 1 which includes an internal reinforcing frame comprising plastic ribs.

5. A surgical abdominal cavity pack for displacing temporarily selected organs within the abdomen during surgery, which pack is nonabrasive, free of foreign bodies and conforms to the organ being displaced, comprising a hollow elongated cylindrical tube having a filler neck at one end of smaller diameter than said tube, said tube being formed from an elastomer having a lubricous hydrogel coating on the external surface thereof, having one structurally flattened side, and being internally reinforced by a frame comprising plastic ribs.

\* \* \* \* \*